United States Patent
Tadanaga et al.

(10) Patent No.: US 10,156,517 B2
(45) Date of Patent: Dec. 18, 2018

(54) $N_2O$ ANALYSIS DEVICE AND ANALYSIS METHOD

(71) Applicants: NIPPON TELEGRAPH AND TELEPHONE CORPORATION, Tokyo (JP); MITSUBISHI HEAVY INDUSTRIES, LTD., Tokyo (JP)

(72) Inventors: Osamu Tadanaga, Tokyo (JP); Akio Tokura, Tokyo (JP); Kenji Muta, Tokyo (JP); Shuuji Fujii, Tokyo (JP); Yoichiro Tsumura, Tokyo (JP); Tatsuyuki Nishimiya, Tokyo (JP)

(73) Assignees: NIPPON TELEGRAPH AND TELEPHONE CORPORATION, Tokyo (JP); MITSUBISHI HEAVY INDUSTRIES, LTD., Tokyo (JP)

(*) Notice: Subject to any disclaimer, the term of this patent is extended or adjusted under 35 U.S.C. 154(b) by 0 days.

(21) Appl. No.: 15/561,701

(22) PCT Filed: Mar. 29, 2016

(86) PCT No.: PCT/JP2016/060003
§ 371 (c)(1),
(2) Date: Sep. 26, 2017

(87) PCT Pub. No.: WO2016/158893
PCT Pub. Date: Oct. 6, 2016

(65) Prior Publication Data
US 2018/0095030 A1 Apr. 5, 2018

(30) Foreign Application Priority Data
Mar. 31, 2015 (JP) .................................. 2015-071378

(51) Int. Cl.
*G01N 21/3504* (2014.01)
*G01N 21/39* (2006.01)
(Continued)

(52) U.S. Cl.
CPC ......... *G01N 21/3504* (2013.01); *G01N 21/39* (2013.01); *G01N 21/85* (2013.01);
(Continued)

(58) Field of Classification Search
CPC ............... G01N 21/3504; G01N 21/85; G01N 2021/3129; G01N 2021/3137;
(Continued)

(56) References Cited

U.S. PATENT DOCUMENTS 5,813,767 A * 9/1998 Calabro' ................. F23N 5/082
250/345
5,838,008 A 11/1998 Esler et al.
(Continued)

FOREIGN PATENT DOCUMENTS

| CN | 102269698 | 12/2011 |
| JP | 2001-506753 | 5/2001 |

(Continued)

OTHER PUBLICATIONS

Tadanaga et al., "Efficient 3-μm difference frequency generation using direct-bonded quasi-phase-matched $LiNbO_3$ ridge waveguides", Applied Physics Letters, 88(6):061101-1-061101-3 (2006).
(Continued)

*Primary Examiner* — Taeho Jo
(74) *Attorney, Agent, or Firm* — Wenderoth, Lind & Ponack, L.L.P.

(57) ABSTRACT

This $N_2O$ analysis device is provided with: a light source (11) which radiates laser light onto an exhaust gas (5) containing $N_2O$, $H_2O$ and $CO_2$; a light receiver (13) which receives the laser light that has been radiated onto the exhaust gas (5); a light source control unit (14a) of a control device (14), which controls the wavelength of the laser light radiated by the light source (11) to between 3.84 μm and 4.00 μm; and a signal analyzing unit (14b) of the control
(Continued)

device (14), which calculates the N₂O concentration by means of infrared spectroscopy, using the laser light received by the light receiver (13) and the laser light controlled by the light source control unit (14a) of the control device (14).

14 Claims, 13 Drawing Sheets

(51) Int. Cl.
*G01N 21/85* (2006.01)
*G01N 21/31* (2006.01)

(52) U.S. Cl.
CPC .............. *G01N 2021/3137* (2013.01); *G01N 2021/3148* (2013.01); *G01N 2021/3185* (2013.01); *G01N 2021/399* (2013.01); *G01N 2021/8578* (2013.01)

(58) Field of Classification Search
CPC ..... G01N 2021/3166; G01N 2021/398; G01N 2027/222; G01N 2021/399; G01N 21/783; G01N 31/224; G01N 33/004
USPC .................................................... 250/339.13
See application file for complete search history.

(56) References Cited

U.S. PATENT DOCUMENTS

| | | | | |
|---|---|---|---|---|
| 6,036,840 | A * | 3/2000 | Christensen ......... | B01D 17/042 205/746 |
| 2001/0014436 | A1* | 8/2001 | Lemelson ............... | F23N 1/022 431/12 |
| 2004/0252300 | A1* | 12/2004 | Slater ....................... | G01J 3/42 356/318 |
| 2006/0013270 | A1* | 1/2006 | Yumoto ................. | G01N 21/39 372/21 |
| 2006/0158648 | A1* | 7/2006 | Matthiessen ....... | G01N 21/3504 356/326 |
| 2007/0241280 | A1 | 10/2007 | Dainobu et al. | |
| 2007/0297465 | A1* | 12/2007 | Yumoto ................. | G01N 21/39 372/21 |
| 2008/0275355 | A1* | 11/2008 | Namjou-Khaless ........................ | A61B 5/0059 600/532 |
| 2010/0058833 | A1* | 3/2010 | Harra ....................... | A61B 5/05 73/23.35 |
| 2011/0150035 | A1* | 6/2011 | Hanson ................... | G01K 11/12 374/161 |
| 2011/0270534 | A1* | 11/2011 | Burba ................. | G01N 21/3504 702/24 |
| 2014/0002823 | A1 | 1/2014 | Nakatani et al. | |
| 2014/0172323 | A1* | 6/2014 | Marino .............. | G01N 21/3504 702/24 |
| 2015/0131700 | A1* | 5/2015 | Chrystie ............... | G01J 5/0014 374/161 |
| 2016/0045841 | A1* | 2/2016 | Kaplan ................ | B01J 19/0093 429/49 |
| 2017/0003218 | A1* | 1/2017 | Sharma ................... | G01N 21/39 |

FOREIGN PATENT DOCUMENTS

| | | |
|---|---|---|
| JP | 2007-501401 | 1/2007 |
| JP | 2007-285823 | 11/2007 |
| JP | 2007-285842 | 11/2007 |
| WO | 98/27416 | 6/1998 |
| WO | 2004/114011 | 12/2004 |
| WO | 2012/120957 | 9/2012 |

OTHER PUBLICATIONS

International Search Report dated Jun. 21, 2016 in International (PCT) Application No. PCT/JP2016/060003, with English Translation.
Written Opinion of the International Searching Authority dated Jun. 21, 2016 in International (PCT) Application No. PCT/JP2016/060003, with English Translation.
Search Report and Written Opinion dated Mar. 16, 2018 in Singapore Application No. 11201707639Y.
Tokura, et al., "Real-Time N₂O Gas Detection System for Agricultural Production Using a 4.6-μm-Band Laser Source Based on a Periodically Poled LiNbO₃ Ridge Waveguide", vol. 13, pp. 9999-10013, Aug. 2013.
Cao et al., "Simultaneous atmospheric nitrous oxide, methane and water vapor detection with a single continuous wave quantum cascade laser", Optics Express, vol. 23, pp. 2121-2132, Jan. 2015.

* cited by examiner

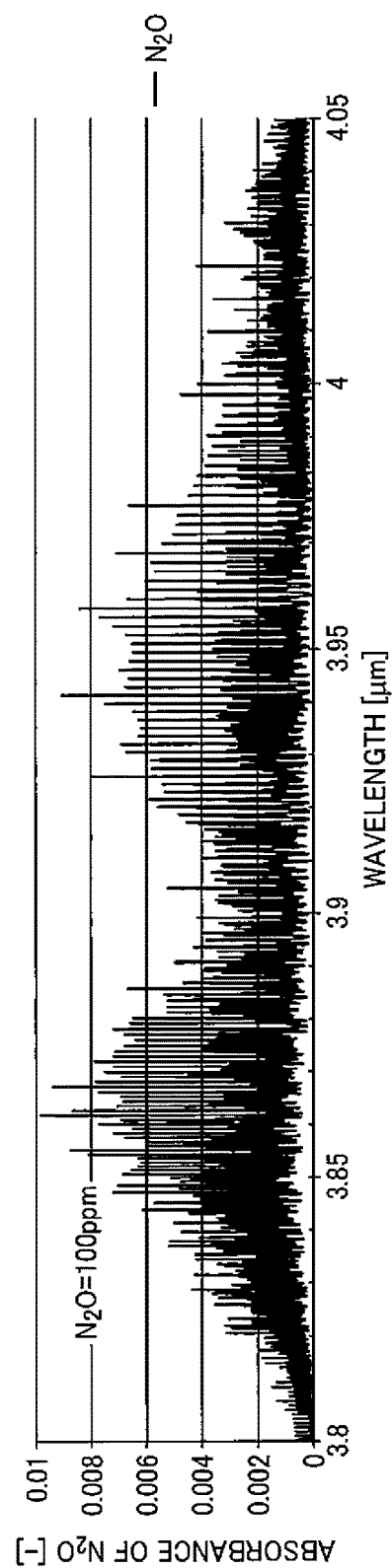

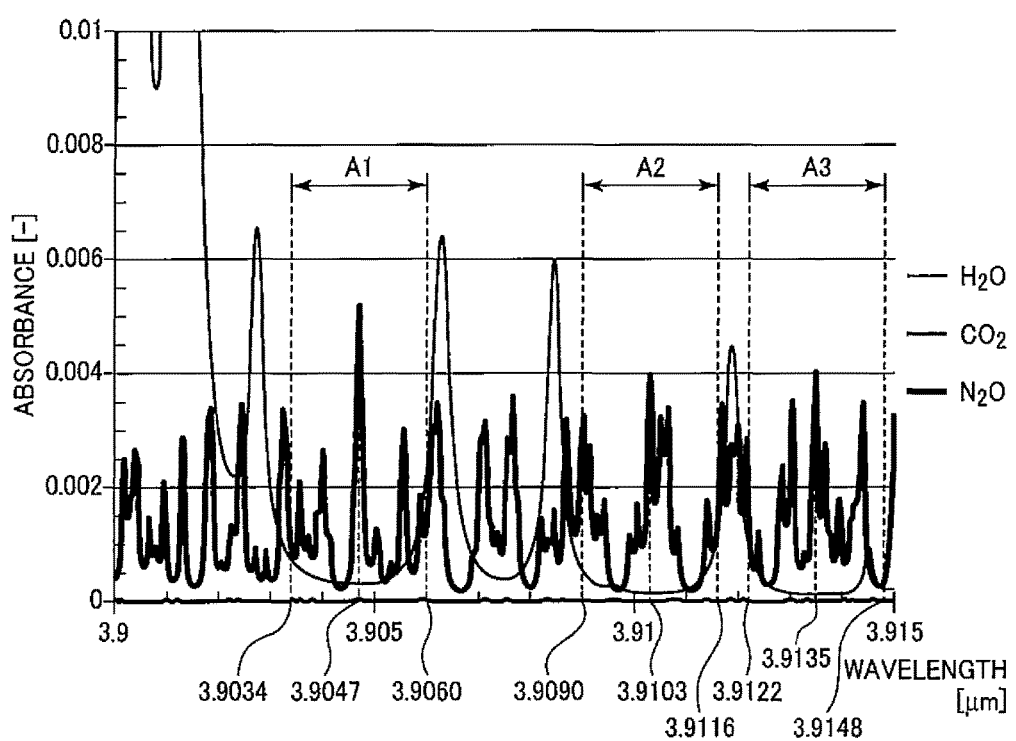

$N_2O$ ANALYSIS DEVICE AND ANALYSIS METHOD

TECHNICAL FIELD

The invention relates to an $N_2O$ analysis device and analysis method.

BACKGROUND ART

Dinitrogen monoxide (hereinafter referred to as $N_2O$) is known to be one of greenhouse gases. However, since it is not subject to a flue gas regulation, the concentration of $N_2O$ in flue gas discharged from sludge incinerators and circulating fluidized bed boilers has not been measured, or control based on the measured concentration of $N_2O$ has not been performed. Since $N_2O$ has about 310 times as much greenhouse effect as carbon dioxide, the reduction of $N_2O$ greatly contributes to the reduction of the total amount of greenhouse gases. Accordingly, it is strongly desired to reduce $N_2O$ discharged from sludge incinerators and circulating fluidized bed boilers as much as possible.

Conventionally, the measurement and analysis of $N_2O$ have been performed with analysis equipment such as a non-dispersive infrared spectrometer, a gas chromatography mass spectrometer (GC-MS), or a gas chromatography electron capture detector (GC-ECD) after gas is sampled and pretreated to remove dust and coexisting gases ($H_2O/CO_2/CO/SO_2/CH_4$ and so on).

In addition, nowadays, a gas analysis device capable of continuously analyzing $NO$, $NO_2$, $N_2O$ and $NH_3$ simultaneously using multiple quantum cascade lasers (hereinafter referred to as QCLs) after gas is sampled and pretreated to remove only dust/$H_2O$, is being developed and researched (for example, refer to Patent Document 1 below).

PRIOR ART DOCUMENT

Patent Document

Patent Document 1: WO2012/120957

Non-Patent Document

Non-Patent Document 1: O. Tadanaga et al., "Efficient 3-μm difference frequency generation using direct-bonded quasi-phase-matched LiNbO3 ridge waveguides", 2006, APPLIED PHYSICS LETTERS, Vol. 88, No. 6, 061101-1-061101-3

SUMMARY OF THE INVENTION

Problems to be Solved by the Invention

However, even the gas analysis device described in Patent Document 1 requires dust removal and dehumidification, and the analysis is performed under a reduced pressure to reduce interference of other coexisting gases. Thus, this gas analysis device has problems of requiring much cost and time. For this reason, it has been strongly desired to directly measure the concentration of $N_2O$ in flue gas without pretreatment.

Moreover, for a QCL utilizing long-wavelength mid-infrared (8 μm), only a material having a high deliquescent property such as $CaF_2$ or $MgF_2$ can be used for window material, which makes it impossible to directly measure combustion flue gas containing a large amount of $H_2O$.

In view of the above, the present invention is made to solve the problems described above, and an object thereof is to provide an $N_2O$ analysis device and analysis method capable of directly measuring the concentration of $N_2O$ in flue gas without pretreatment.

Means for Solving the Problems

To solve the above problems, an $N_2O$ analysis device according to a first aspect of the invention comprises light emission means for emitting laser light to flue gas containing $N_2O$, $H_2O$, and $CO_2$; light reception means for receiving the laser light emitted to the flue gas; wavelength control means for performing control such that a wavelength of the laser light emitted by the light emission means is in a 3.84 to 4.00 μm band; and $N_2O$ concentration calculation means for calculating a concentration of $N_2O$ by means of infrared spectroscopy, using the laser light received by the light reception means and the laser light controlled by the wavelength control means.

To solve the above problems, an $N_2O$ analysis device according to a second aspect of the invention is the $N_2O$ analysis device according to the first aspect of the invention, wherein the wavelength control means performs control such that the wavelength of the laser light is 3.9034 to 3.9060 μm, 3.9090 to 3.9116 μm, or 3.9122 to 3.9148 μm.

To solve the above problems, an $N_2O$ analysis device according to a third aspect of the invention is the $N_2O$ analysis device according to the first or second aspect of the invention, wherein the wavelength control means performs control such that the wavelength of the laser light is 3.9047 μm, 3.9103 μm, or 3.9135 μm.

To solve the above problems, an $N_2O$ analysis device according to a fourth aspect of the invention is the $N_2O$ analysis device according to any one of the first to third aspects of the invention, wherein the light emission means includes a nonlinear optical crystal, generates, by means of difference frequency generation using inputs of laser light with a wavelength of $\lambda_1$ and laser light with a wavelength of $\lambda_2$, laser light with a wavelength of $\lambda_3$ satisfying $1/\lambda_3 = 1/\lambda_1 - 1/\lambda_2$, and outputs the laser light with the wavelength of $\lambda_3$.

To solve the above problems, an $N_2O$ analysis device according to a fifth aspect of the invention is the $N_2O$ analysis device according to any one of the first to fourth aspects of the invention, further comprising temperature measurement means for measuring a temperature of the flue gas, wherein the $N_2O$ concentration calculation means calculates the concentration of $N_2O$ by means of the infrared spectroscopy, using also the temperature of the flue gas measured by the temperature measurement means.

To solve the above problems, an $N_2O$ analysis device according to a sixth aspect of the invention is the $N_2O$ analysis device according to any one of the first to fifth aspects of the invention, further comprising sampling means for sampling the flue gas, wherein the light emission means emits the laser light to the flue gas sampled by the sampling means.

To solve the above problems, an $N_2O$ analysis device according to a seventh aspect of the invention is the $N_2O$ analysis device according to the sixth aspect of the invention, further comprising heating means for heating the flue gas sampled by the sampling means.

To solve the above problems, an $N_2O$ analysis method according to an eighth aspect of the invention comprises emitting, by light emission means, laser light with a wavelength of 3.84 to 4.00 μm to flue gas containing $N_2O$, $H_2O$, and $CO_2$;

receiving the laser light emitted to the flue gas; and calculating a concentration of $N_2O$ by means of infrared spectroscopy, using the received laser light and the laser light which is controlled to be 3.84 to 4.00 μm.

To solve the above problems, an $N_2O$ analysis method according to a ninth aspect of the invention is the $N_2O$ analysis method according to the eighth aspect of the invention, wherein the wavelength of the laser light emitted by the light emission means is controlled to be 3.9034 to 3.9060 μm, 3.9090 to 3.9116 μm, or 3.9122 to 3.9148 μm.

To solve the above problems, an $N_2O$ analysis method according to a tenth aspect of the invention is the $N_2O$ analysis method according to the eighth or ninth aspect of the invention, wherein the wavelength of the laser light emitted by the light emission means is controlled to be 3.9047 μm, 3.9103 μm, 3.9135 μm.

To solve the above problems, an $N_2O$ analysis method according to an eleventh aspect of the invention is the $N_2O$ analysis method according to any one of the eighth to tenth aspects of the invention, wherein equipment including a nonlinear optical crystal is used for the light emission means, the equipment generating, by means of difference frequency generation using inputs of laser light with a wavelength of $\lambda_1$ and laser light with a wavelength of $\lambda_2$, laser light with a wavelength of $\lambda_3$ satisfying $1/\lambda_3=1/\lambda_1-1/\lambda_2$, and outputting the laser light with the wavelength of $\lambda_3$.

To solve the above problems, an $N_2O$ analysis method according to a twelfth aspect of the invention is the $N_2O$ analysis method according to any one of the eighth to eleventh aspects of the invention, further comprising: measuring a temperature of the flue gas; and calculating the concentration of $N_2O$ by means of the infrared spectroscopy, using also the measured temperature of the flue gas.

To solve the above problems, an $N_2O$ analysis method according to a thirteenth aspect of the invention is the $N_2O$ analysis method according to any one of the eighth to twelfth aspects of the invention, wherein the flue gas to which the laser light is emitted is sampled.

To solve the above problems, an $N_2O$ analysis method according to a fourteen aspect of the invention is the $N_2O$ analysis method according to the thirteenth aspect of the invention, wherein the sampled flue gas is heated.

Effect of the Invention

The present invention makes it possible to measure the concentration of $N_2O$ in the flue gas accurately and promptly without pretreatment.

BRIEF DESCRIPTION OF THE DRAWINGS

FIG. 6C is a graph illustrating the absorbance of $N_2O$ in the wavelength band of 3.9 μm at 800° C.

FIG. 7 is a graph illustrating the absorbance of $H_2O$, $CO_2$, $N_2O$ around the wavelength 3.9 μm at 800° C.

MODE FOR CARRYING OUT THE INVENTION

Descriptions will be provided for embodiments of an $N_2O$ concentration analysis device and analysis method according to the present invention based on the drawings. However, the present invention is not limited only to the following embodiments described based on the drawings.

[First Embodiment]

Descriptions will be provided using FIGS. 1, 2, 3, 4A to 4C, 5, 6A to 6C, and 7 for an application of an $N_2O$ concentration analysis device according to a first embodiment of the present invention to $N_2O$ measurement in a sludge incinerator.

Figure 1:
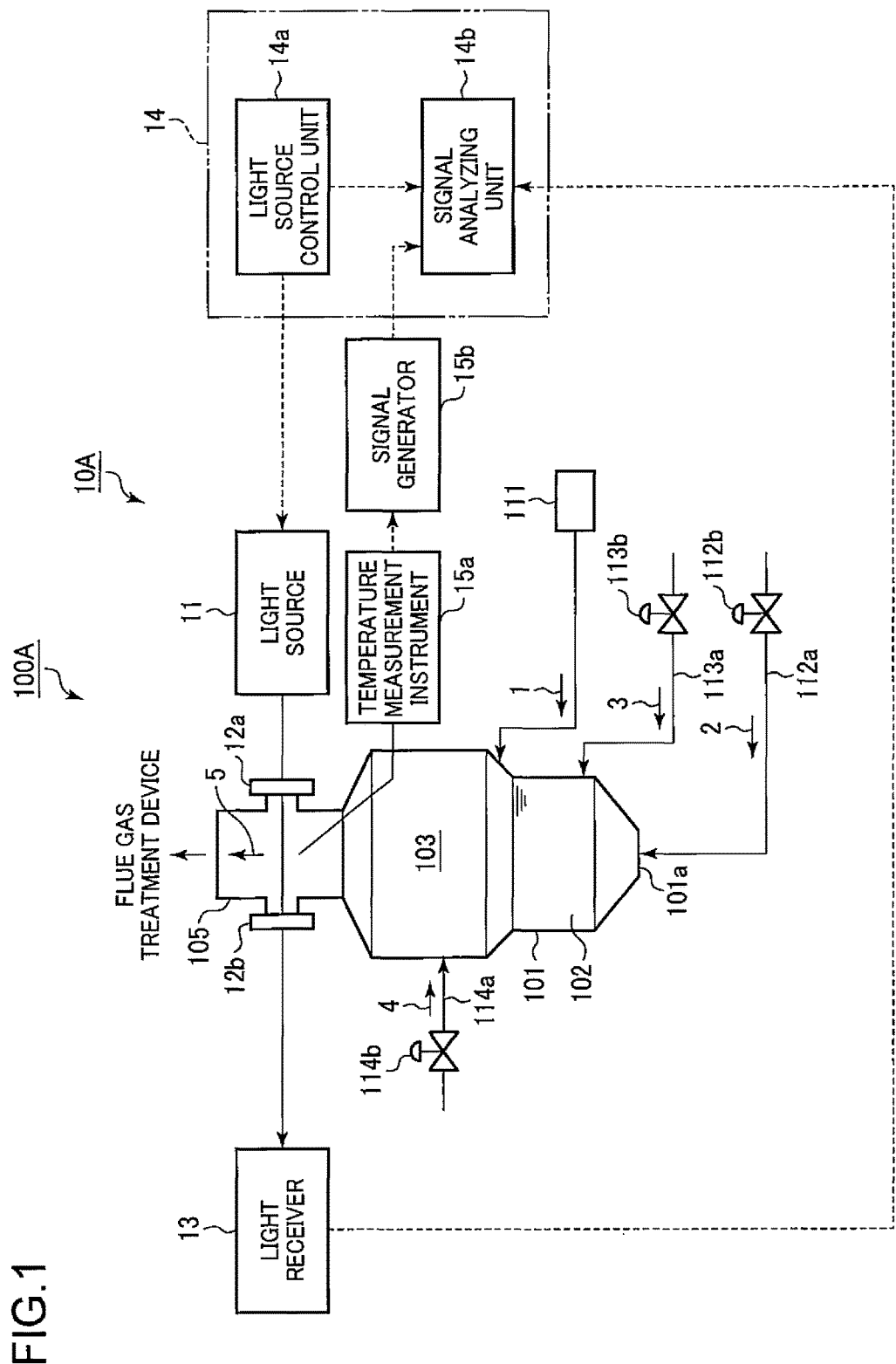
FIG. 1 is a schematic configuration diagram of a sludge incinerator including an $N_2O$ concentration analysis device according to a first embodiment of the present invention.

As illustrated in FIG. 1, a sludge incinerator 100A according to this embodiment is a fluidized bed incinerator in which sludge (fuel) 1 is supplied into a sludge incinerator main body 101 by a sludge feeder (feeder) 111, and inside the sludge incinerator main body 101, a fluidized bed 102 is formed by sand grains (fluidized material) as a heating medium together with the sludge 1 and combusts. Combustion air 2 with its temperature adjusted is introduced from a bottom 101a of the sludge incinerator main body 101 by means of a combustion air supply pipe 112a and a combustion air supply flow rate adjustment valve 112b, and auxiliary fuel 3 is introduced into the fluidized bed 102 in the sludge incinerator main body 101 by means of an auxiliary fuel supply pipe 113a and an auxiliary fuel supply flow rate adjustment valve 113b, and then combusts. The sand grains in the heated fluidized bed 102 are moved and combusted together with the supplied sludge 1 by the combustion air 2 and generated combustion gas. Further, while the combustion gas of sludge moves up in a freeboard 103 above the fluidized bed 102, combustion of the combustion gas is completed with secondary air 4 supplied by means of a secondary air supply pipe 114a and a secondary air supply flow rate adjustment valve 114b. Then, flue gas 5 after the combustion passes through a flue 105 at an upper portion of the sludge incinerator main body 101 and is discharged to a flue gas treatment device.

The sludge incinerator 100A includes an $N_2O$ concentration analysis device 10A for analyzing the concentration of $N_2O$ in the flue gas 5 passing through the flue 105.

As illustrated in FIG. 1, the $N_2O$ concentration analysis device 10A includes a light source 11, windows 12a and 12b, a light receiver 13, a control device 14, a temperature measurement instrument 15a, and a signal generator 15b. The control device 14 includes a light source control unit 14a and a signal analyzing unit 14b which calculates the concentration of $N_2O$ based on a light reception signal from the light receiver 13, a temperature signal from the signal generator 15b, and a reference signal from the light source control unit 14a.

Figure 2:
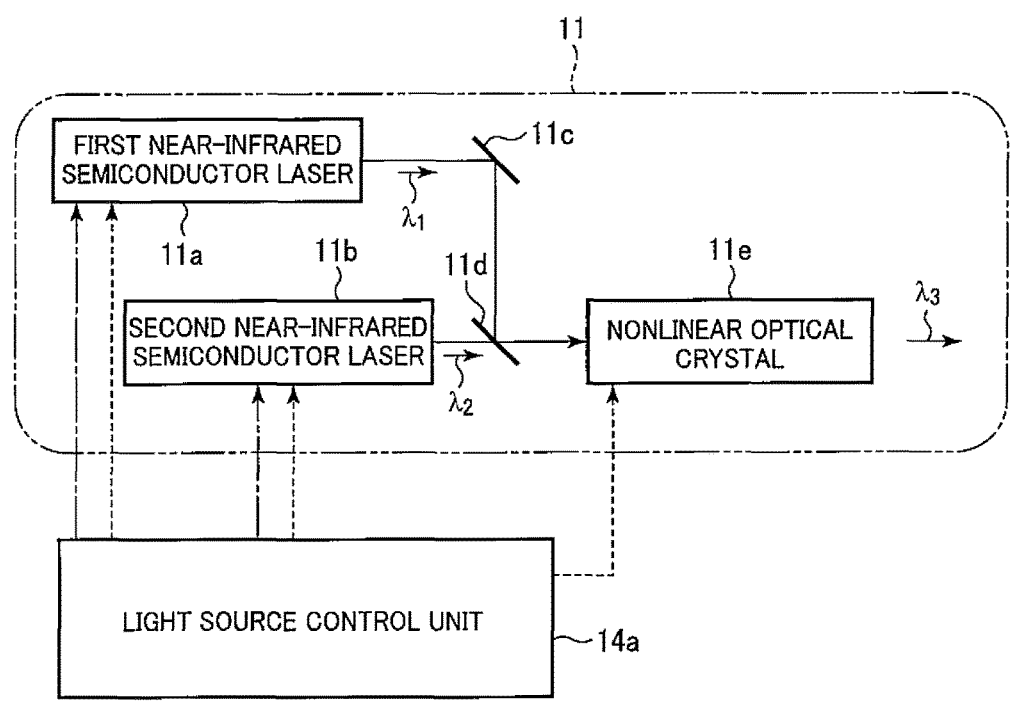
FIG. 2 is a schematic configuration diagram of an example of laser light source and a wavelength control device included in the $N_2O$ concentration analysis device.

Here, descriptions will be provided for an example of the light source 11 and the light source control unit 14a, using FIG. 2.

As illustrated in FIG. 2, the light source 11 includes the two near-infrared semiconductor lasers (hereinafter referred to as NIR-LDs) 11a and 11b having different oscillation wavelengths, a mirror (reflection mirror) 11c, a multiplexer 11d, and a nonlinear optical crystal 11e. In the light source 11 thus configured, laser light having a wavelength $\lambda_1$ generated from the first (one) NIR-LD 11a is inputted into the nonlinear optical crystal 11e via the mirror 11c and the multiplexer 11d, and at the same time, laser light having a wavelength $\lambda_2$ ($\lambda_2 > \lambda_1$) generated from the second (the other) NIR-LD 11b is inputted into the nonlinear optical crystal 11e via the multiplexer 11d. As a result, the light source 11 emits laser light having a short-wavelength mid-infrared wavelength $\lambda_3$ ($1/\lambda_3 = 1/\lambda_1 - 1/\lambda_2$), which is the difference-frequency light. This difference frequency generation is based on the second order nonlinear optical effect and occurs in a second order nonlinear optical crystal. As second order nonlinear optical crystals, lithium niobate (LN), lithium tantalate (LT), and potassium titanyl phosphate (KTP) which have large nonlinear constants are well known.

In addition, to utilize the nonlinear constant efficiently, the phases of the wavelengths $\lambda_1$, $\lambda_2$, and $\lambda_3$ of the incident and outgoing laser lights need to be matched, and the angle matching method or the quasi phase matching method are used for it. For example, as shown in Non-Patent Document 1, LN is used as a nonlinear optical crystal, a periodic polarization reversal structure is adopted to achieve the quasi phase matching, and a waveguiding structure is further adopted to generate a mid-infrared light in a 3 μm band with high efficiency. Although in Non-Patent Document 1, light of a 3 μm band is generated, for example, it is possible to generate a short-wavelength mid-infrared light with a desired wavelength $\lambda_3$ in a 2 to 5 μm range, by appropriately selecting the wavelength $\lambda_1$ and the wavelength $\lambda_2$, which are in the near-infrared range.

In this case, the stability/robustness of the device is guaranteed by using NIR-LD light sources, which have been used for many applications for communication or the like, for the original light sources. In addition, in a QCL that oscillates and generates a long-wavelength mid-infrared light, since the wavelength line width of the generated laser light is wide, the measurement tends to be affected by coexisting gases. On the other hand, since in this embodiment, the NIR-LDs, the wavelength line widths of which are extremely narrow, are used as origins, the wavelength line width of the generated short-wavelength mid-infrared laser light is as narrow as the NIR-LDs, and this embodiment has a characteristic of being hardly affected by coexisting gases.

Note that although the incident lights from the two NIR-LDs 11a and 11b enter the nonlinear optical crystal 11e through the spatial optical system in FIG. 2, optical fibers can be used for the incidence.

The light source 11 is controlled by the light source control unit 14a, which performs temperature control for the two NIR-LDs 11a and 11b and the nonlinear optical crystal 11e, and electric current control for the two NIR-LDs 11a and 11b. Appropriate setting of the temperature allows for precise control of the oscillation wavelengths at the NIR-LDs 11a and 11b, and precise control of combinations of wavelengths that can be efficiently generated by the difference frequency generation, at the nonlinear optical crystal 11e.

Further, in this embodiment, utilizing short-wavelength mid-infrared (around 4 μm) for the measurement wavelength allows sapphire window plates having high strength/corrosion resistance to be utilized for the windows 12a and 12b. On the other hand, since, in a QCL utilizing long-wavelength mid-infrared (8 μm), only $CaF_2$, $MgF_2$, or the like having a high deliquescent property can be used for window material, it is impossible to directly measure combustion flue gas containing a large amount of $H_2O$.

Meanwhile, strong basic absorption of $N_2O$ exists at a wavelength of 4.50 μm (absorption intensity $1 \times 10^{-18}$ cm/molecule), and typically, $N_2O$ is observed as a target in a wavelength region where such strong absorption exists. However, in the application described above, for example, where gases such as 50% of water and 12% of carbon dioxide coexist, for example, even though a strong absorption of $N_2O$ exists, it is impossible to measure the absorption line accurately because the absorption of $N_2O$ is small compared to the coexisting gases and the coexisting gases obstruct (interfere) the measurement.

After diligent studies in this respect, it was found that absorption of $N_2O$ can be observed at around 3.9 μm while avoiding influence of the coexisting gases, even though the absorption intensity is $2.5 \times 10^{-20}$ cm/molecule, which is a small absorbance compared to the basic absorption. The situation will be described using FIGS. 3, 4A to 4C, 5, 6A to 6C, and 7.

Figure 3:
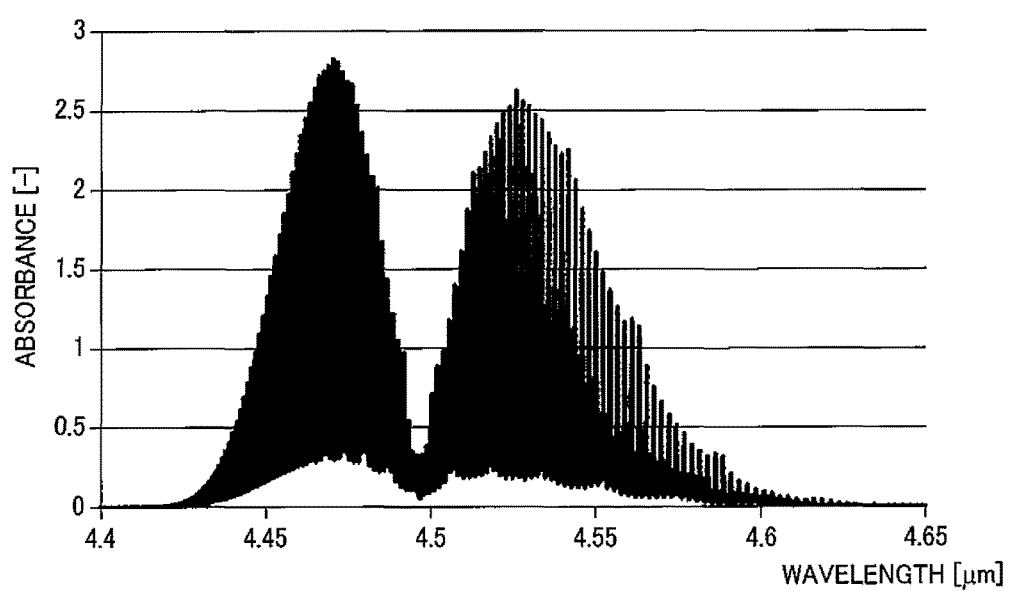
FIG. 3 is a graph illustrating the absorbance of $N_2O$ in a wavelength band of 4.5 μm at room temperature.
Figure 4A:
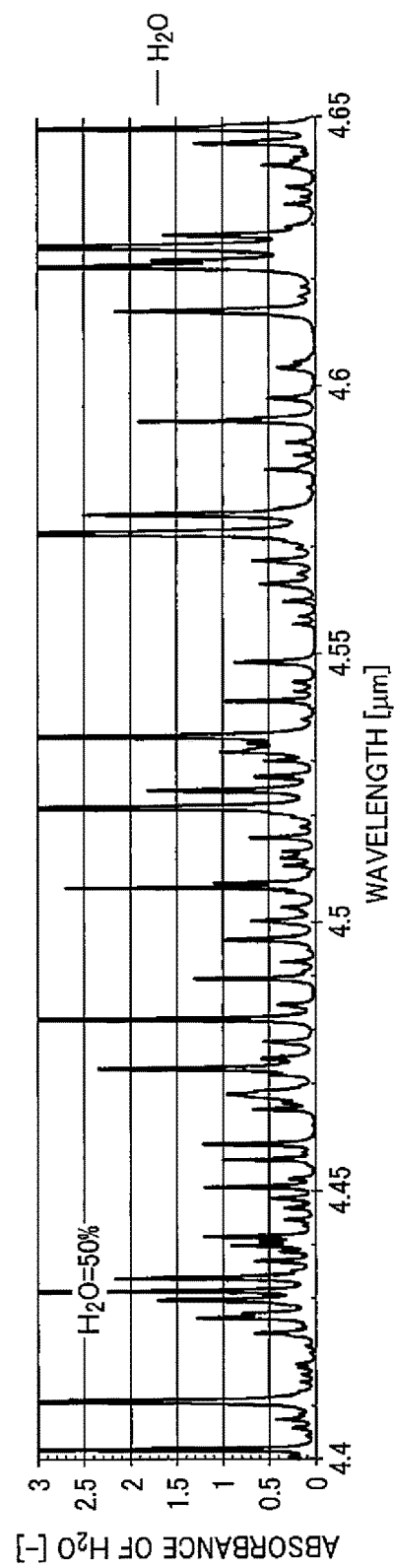
FIG. 4A is a graph illustrating the absorbance of $H_2O$ in the wavelength band of 4.5 μm at 800° C.
Figure 4B:
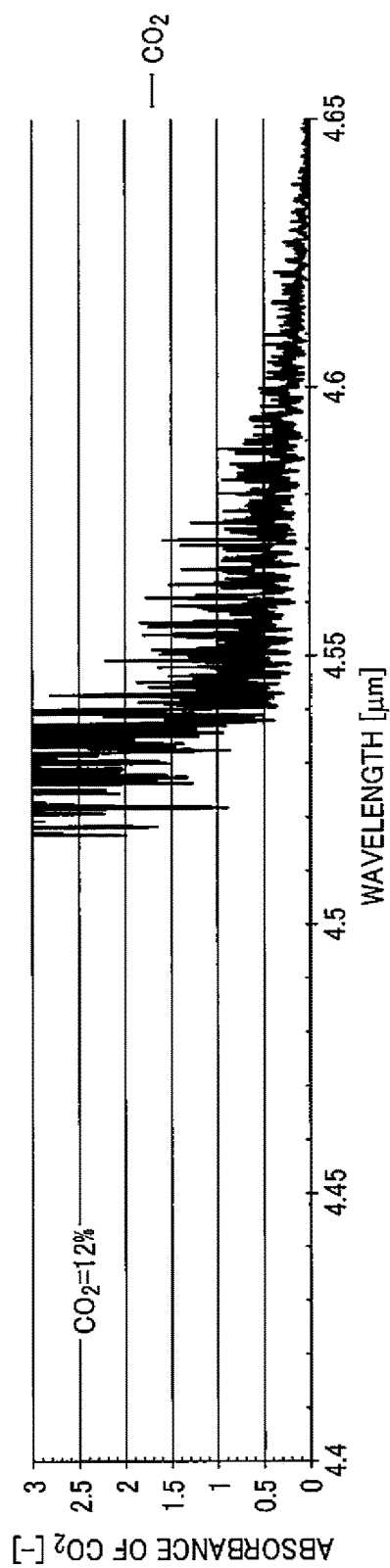
FIG. 4B is a graph illustrating the absorbance of $CO_2$ in the wavelength band of 4.5 μm at 800° C.
Figure 4C:
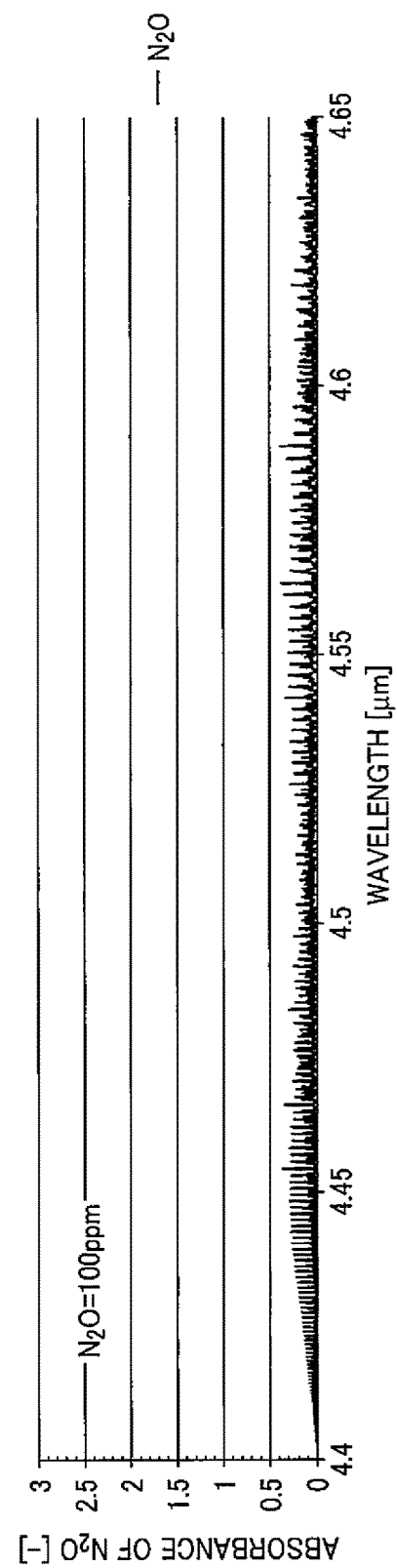
FIG. 4C is a graph illustrating the absorbance of $N_2O$ in the wavelength band of 4.5 μm at 800° C.

FIG. 3 illustrates the absorbance of $N_2O$ around 4.5 μm. FIG. 3 illustrates the case where the concentration of $NO_2$ is 100 ppm, the pressure is 1 atmospheric pressure, the path length is 6m, and the temperature is room temperature. FIG. 3 shows that, depending on the wavelength in this region, there is strong absorption the absorbance of which exceeds 1. FIGS. 4A to 4C show the absorbance around a 4.5 μm band for the case where the temperature is 800° C., which is an example of a temperature assumed to be inside the incinerator, and where 50% of water and 12% of $CO_2$ coexist. According to FIGS. 4A to 4C, it was confirmed that in the high temperature condition at 800° C., the absorbance of $N_2O$ reduces while the absorption of $CO_2$, which is a coexisting gas, is very strong, which makes it difficult to observe $N_2O$. Note that according to FIG. 4B, the absorbance of $CO_2$ is larger than 1 at wavelengths of 4.52 μm or less.

Figure 5:
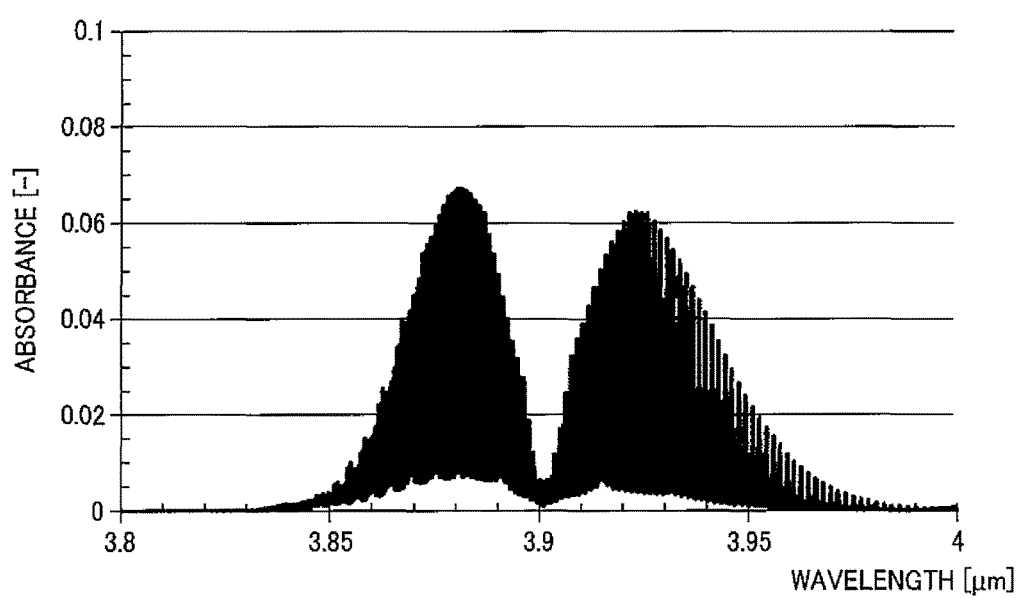
FIG. 5 is a graph illustrating the absorbance of $N_2O$ in a wavelength band of 3.9 μm at room temperature.
Figure 6A:
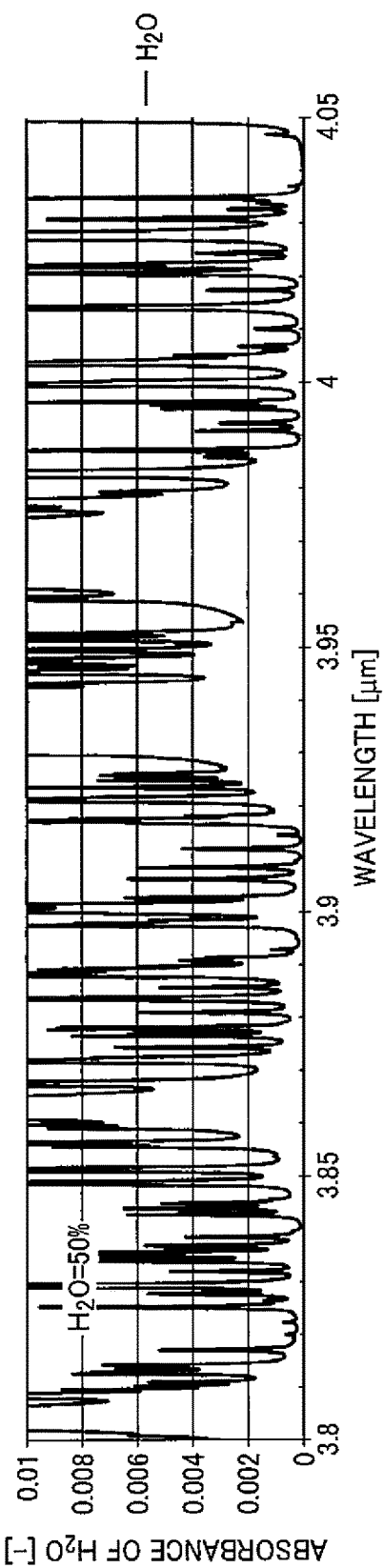
FIG. 6A is a graph illustrating the absorbance of $H_2O$ in the wavelength band of 3.9 μm at 800° C.
Figure 6B:
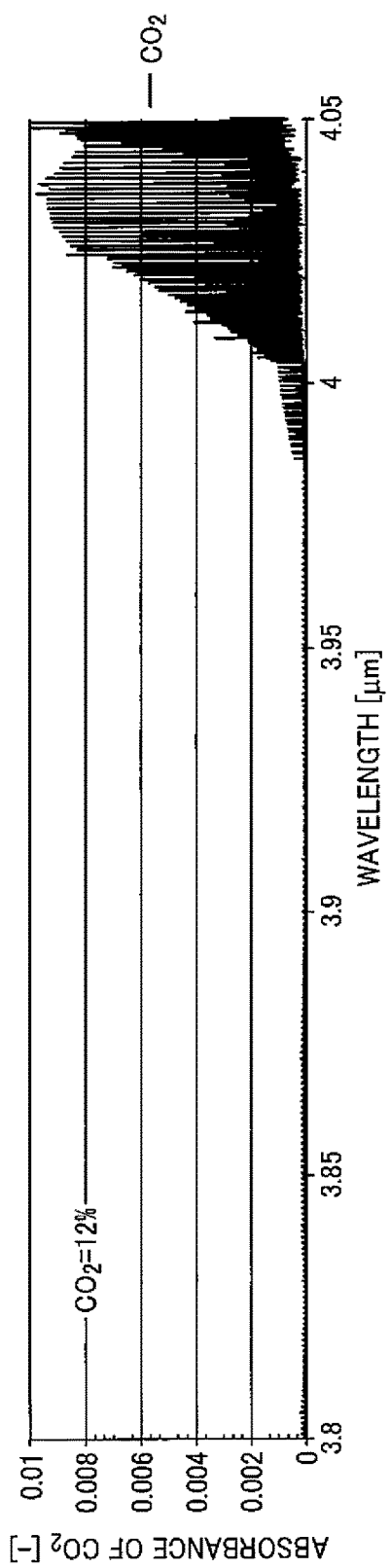
FIG. 6B is a graph illustrating the absorbance of $CO_2$ in the wavelength band of 3.9 μm at 800° C.

Meanwhile, FIG. 5 shows the absorbance of $N_2O$ around 3.9 μm for the case where the concentration of $N_2O$ is 100 ppm, the pressure is 1 atmospheric pressure, the path length is 6 m, the temperature is room temperature. It is shown that the absorbance of $N_2O$ is only about one fortieth of the absorbance around 4.5 μm. In the same way as in FIGS. 4A to 4C, FIGS. 6A to 6C show the absorbance around a 3.9 μm band for the case where the temperature is 800° C., which is an example of a temperature assumed to be inside the incinerator, and where 50% of water and 12% of $CO_2$ coexist. From FIGS. 6A to 6C, it was confirmed that unlike the vicinity of 4.5 μm, this region is less susceptible to the absorption of $CO_2$. FIG. 7 illustrates the case where FIGS. 6A to 6C are superimposed and the scale of the vertical axis is changed. According to FIG. 7, it was confirmed that although the absorption of water exists around 3.9 μm, the positions of its absorption lines are sparse and the influence of the absorption lines of water is small, and it is possible to observe $N_2O$.

From this result, the light source 11 is a mid-infrared semiconductor laser capable of emitting laser light with, for example, a vibrational-rotational absorption wavelength of $N_2O$ in a wavelength band of 3.84 to 4.00 μm, preferably a wavelength region A1 (wavelengths of 3.9034 to 3.9060 μm), a wavelength region A2 (wavelengths of 3.9090 to 3.9116 μm), or a wavelength region A3 (wavelengths of 3.9122 to 3.9148 μm), or more preferably a wavelength of 3.9047 μm, a wavelength of 3.9103 μm, or a wavelength of 3.9135 μm.

The windows 12a and 12b are arranged to face each other at the flue 105 and can be passed through by the laser light. It is preferable that the windows 12a and 12b are made of, for example, sapphire. This is because that sapphire does not have a deliquescent property and eliminates the need of maintenance such as replacing the windows.

The light receiver 13 receives the laser light emitted by the light source 11 and having passed through the window 12a, the flue 105, and the window 12b. A light intensity signal (light reception signal) obtained by the light receiver 13 is outputted to the signal analyzing unit 14b to be described in detail later of the control device 14.

The temperature measurement instrument 15a is disposed so as to measure the temperature at generally the same position as the laser measurement position in the flue 105, and capable of measuring the temperature of the flue gas 5 flowing inside the flue 105. The temperature measurement instrument 15a measures the temperature of the flue gas 5, and the temperature signal generated by the signal generator 15b is outputted to the signal analyzing unit 14b.

The light source control unit 14a transmits a control signal to the light source 11 to control the wavelength of the laser light emitted by the light source 11, and transmits the reference signal to the signal analyzing unit 14b. The reference signal is a signal having the wavelength information of the laser light emitted by the light source 11 based on the control signal.

The signal analyzing unit 14b calculates the concentration of $N_2O$ and outputs a signal corresponding to this concentration of $N_2O$. The signal analyzing unit 14b calculates the concentration of $N_2O$ by means of infrared spectroscopy based on the reference signal transmitted from the light source control unit 14a, the light reception signal obtained at the light receiver 13, and the temperature signal transmitted from the temperature measurement instrument 15a via the signal generator 15b.

Figure 8:
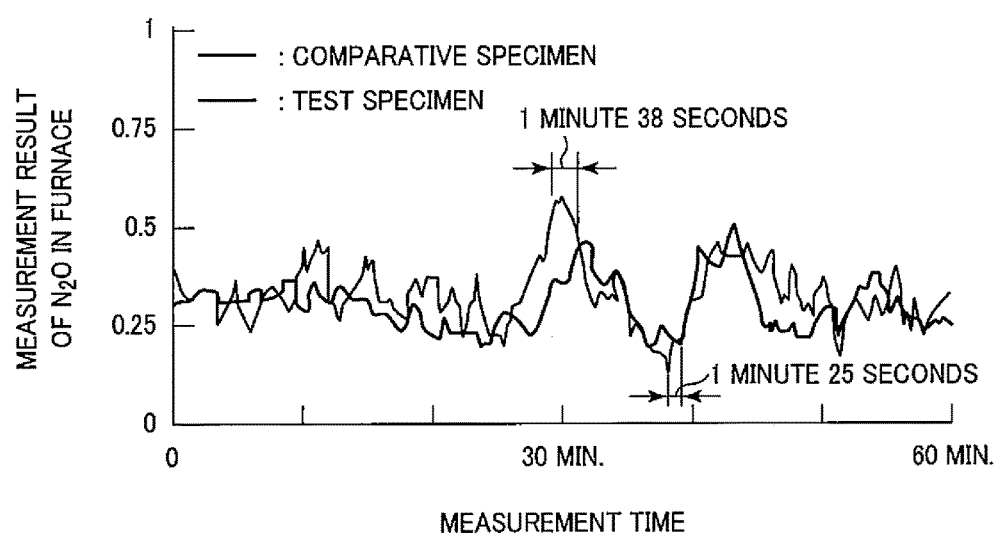
FIG. 8 is a graph illustrating the relationship between the measurement time and the measurement result of the $N_2O$ concentration analysis device.

The measurement time of the $N_2O$ concentration analysis device 10A described above and the measurement result of the concentration of $N_2O$ will be described using FIG. 8. In FIG. 8, the test specimen indicates a case of the $N_2O$ concentration analysis device according to this embodiment, and the comparative specimen indicates a case of a conventional $N_2O$ concentration analysis device that measures the concentration of $N_2O$ after flue gas is sampled and pretreated to remove dust and coexisting gases. In FIG. 8, the thin line indicates the measurement result of the test specimen, and the thick line indicates the measurement result of the comparative specimen. The measured gas contained 50% of water, 12% of $CO_2$, several % of $O_2$, and the temperature of the gas was 800 to 850° C.

As illustrated in FIG. 8, for the maximum peaks of the concentrations of $N_2O$ around 30 minutes, it was found that the test specimen was able to be measured 1 minute and 38 seconds before the case of the comparative specimen. It was also found that the concentration of $N_2O$ of the test specimen was higher than that for the case of the comparative specimen. For the minimum values of the concentrations of $N_2O$ around 40 minutes, it was found that the test specimen was able to be measured 1 minute and 25 seconds before the case of the comparative specimen. It was also found that the concentration of $N_2O$ of the test specimen is lower than that for the case of the comparative specimen. In other words, it was confirmed that the $N_2O$ concentration analysis device 10A according to this embodiment makes it possible to analyze the concentration of $N_2O$ promptly and accurately compared to a conventional $N_2O$ concentration analysis device regardless of the maximum value and the minimum values of the concentration of $N_2O$.

Thus, the $N_2O$ concentration analysis device 10A according to this embodiment, having the equipment described above, can directly measure the concentration of $N_2O$ in the flue gas 5 without pretreatment of removing dust and coexisting gases other than $N_2O$ in the flue gas 5, which makes it possible to measure the concentration of $N_2O$ in the flue gas 5 promptly and accurately.

In addition, changing the attachment positions of the windows 12a and 12b allows for the measurement at an upstream portion such as the inside of the freeboard 103 where the concentration of particles is high, or a position directly above the fluidized bed where flames cross and the concentration of $N_2O$ is high. Moreover, in the measurement at a downstream portion, the concentration of $N_2O$ measured by the $N_2O$ concentration analysis device 10A according to this embodiment shows an average value on the laser light path. For this reason, although conventional sampling measurement requires traverse measurement or the like to find a representative value when the concentration is not constant inside the flue, the $N_2O$ concentration analysis method in accordance with the $N_2O$ concentration analysis device 10A according to this embodiment makes it possible to always measure the average concentration of $N_2O$ in the flue 105.

[Second Embodiment]

Figure 9:
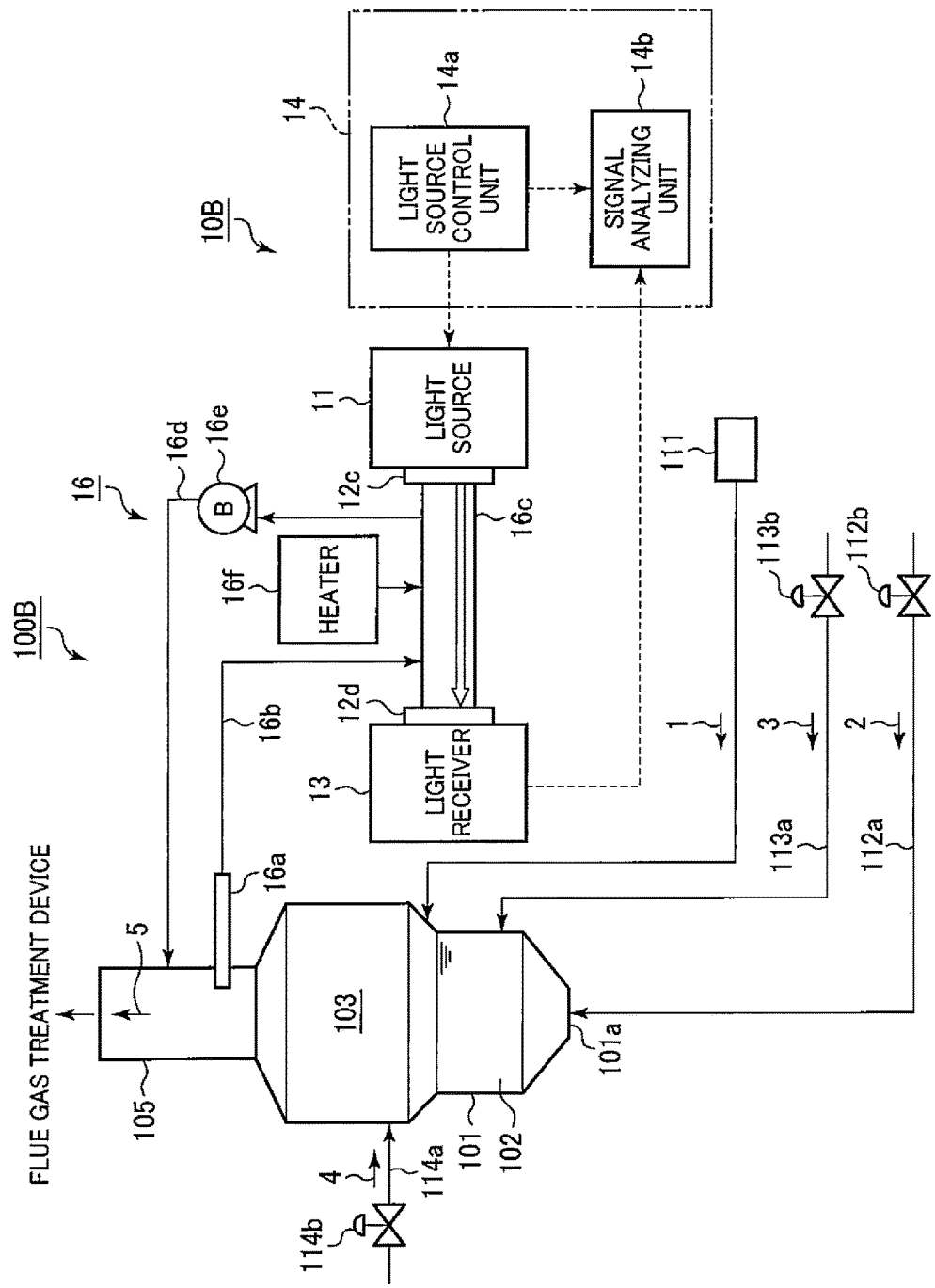
FIG. 9 is a schematic configuration diagram of an $N_2O$ concentration analysis device according to a second embodiment of the present invention.

Descriptions will be provided for an application of the measurement of $N_2O$ in a sludge incinerator in accordance with a $N_2O$ concentration analysis device according to a second embodiment of the present invention using FIG. 9.

In this embodiment, a sampling device is added to the $N_2O$ concentration analysis device according to the first embodiment described above, and except for it, this embodiment is generally the same as the first embodiment.

As illustrated in FIG. 9, a sludge incinerator 100B according to this embodiment includes the same equipment as in the sludge incinerator 100A according to the above first embodiment, and also includes an $N_2O$ concentration analysis device 10B.

The $N_2O$ concentration analysis device 10B includes the same equipment as in the $N_2O$ concentration analysis device 10A according to the above first embodiment, and further includes a sampling device 16. The sampling device 16 includes a sampling pipe 16a, a delivery pipe 16b, a sampling cell 16c, a discharge pipe 16d, and a blower 16e.

The sampling pipe 16a is disposed with its distal end side protruded into the flue 105, and samples the flue gas 5 flowing through the flue 105.

The proximal end side of the delivery pipe 16b is connected to the proximal end side of the sampling pipe 16a, and the distal end side of the delivery pipe 16b is connected to the proximal end side (the end side connected to the light receiver 13) of the sampling cell 16c.

The distal end of the sampling cell 16c is coupled to the light source 11 through a window 12c, and the proximal end of the sampling cell 16c is coupled to the light receiver 13 through a window 12d. Note that it is preferable that the windows 12c and 12d be made of, for example, sapphire in the same way as in the windows 12a and 12b.

The proximal end of the discharge pipe 16d is connected to the distal end side (the end side connected to the light source 11) of the sampling cell 16c, and the distal end of the discharge pipe 16d is connected to the flue 105 downstream of the sampling pipe 16a in the flowing direction of the flue gas. The blower 16e is disposed in the middle of the discharge pipe 16d. With the operation of this blower 16e, a part of the flue gas 5 flowing through the flue 105 will be introduced through the sampling pipe 16a and the delivery pipe 16b into the sampling cell 16c, and the flue gas 5 having flowed through the sampling cell 16c will be returned through the discharge pipe 16d to the flue 105.

The sampling device 16 further includes a heater 16f that heats the sampling cell 16c to keep the temperature of the flue gas 5 inside the sampling cell 16c at a desired temperature. This allows the inside of the sampling cell 16c to be kept at a predetermined constant temperature, and makes it possible to measure the concentration of $N_2O$ in the flue gas 5 without measuring the temperature.

Here, the main operation of the above $N_2O$ concentration analysis device 10B will be described. Note that the main operation of the sludge incinerator 100B is the same as that of the above sludge incinerator 100A, and descriptions thereof are omitted.

First, the heater 16f is activated to heat the sampling cell 16c. This keeps the inside of the sampling cell 16c at a constant temperature, making it possible to keep a temperature correction constant when directly measuring the concentration of $N_2O$ in the flue gas 5 flowing through the flue 105, and thereby eliminating the need for a temperature measurement instrument and its signal generator.

Then, the blower 16e is activated. This will cause a part of the flue gas 5 flowing through the flue 105 to flow into the sampling cell 16c through the sampling pipe 16a and the delivery pipe 16b.

Next, the light source 11 emits laser light with a wavelength of a predetermined range (for example, 3.84 to 4.00 µm) based on a control signal from the light source control unit 14a of the control device 14. The laser light is received by the light receiver 13 through the window 12c, the flue gas 5 inside the sampling cell 16c, and the window 12d. The light receiver 13 transmits the light reception signal corresponding to the received laser light to the signal analyzing unit 14b of the control device 14. The signal analyzing unit 14b also receives the reference signal from the light source control unit 14a.

The signal analyzing unit 14b calculates the concentration of $N_2O$ in the flue gas by means of infrared spectroscopy based on the light reception signal and the reference signal.

Thus, even in the case where the flue gas 5 is sampled, the $N_2O$ concentration analysis device 10B according to this embodiment including the above equipment makes it possible to directly measure the concentration of $N_2O$ in the flue gas without removing dust and coexisting gasses other than $N_2O$ in the flue gas 5, which makes it possible to measure the concentration of $N_2O$ in the flue gas 5 promptly and accurately.

Moreover, the $N_2O$ concentration analysis device 10B allows for the installment without a large-scale modification work such as attaching measurement windows to a furnace.

[Other Embodiments]

In the above, descriptions have been provided for the case where the concentration of $N_2O$ in the flue gas containing 100 ppm of $N_2O$, 50% of $H_2O$, and 12% of $CO_2$ is measured. However, the concentration of $N_2O$ in the flue gas is not limited to 100 ppm. When the concentration of $N_2O$ is higher than 100 ppm, the absorbance of laser is high, and accordingly, it is possible to obtain the same operation effect as described above.

In addition, although in the above, descriptions have been provided for the case where the concentration of $N_2O$ in the flue gas containing 100 ppm of $N_2O$, 50% of $H_2O$, and 12% of $CO_2$ is measured, the concentration of $H_2O$ in the flue gas is not limited to 50%. When the concentration of $H_2O$ is lower than 50%, the absorbance of laser is lower than in the case where the concentration of $H_2O$ is 50%, and the influence on the measurement of the concentration of $N_2O$ is small. Accordingly, it is possible to obtain the same operation effect as described above.

Moreover, although in the above, descriptions have been provided for the case where the concentration of $N_2O$ in the flue gas containing 100 ppm of $N_2O$, 50% of $H_2O$, and 12% of $CO_2$ is measured, the concentration of $CO_2$ in the flue gas is not limited to 12%. When the concentration of $CO_2$ is lower than 12%, the absorbance of laser is lower than in the case where the concentration of $CO_2$ is 12%, and the influence on the measurement of the concentration of $N_2O$ is small. Accordingly, it is possible to obtain the same operation effect as described above.

INDUSTRIAL APPLICABILITY

Since the $N_2O$ analysis device and analysis method according to the present invention can measure the concentration of $N_2O$ in the flue gas accurately and promptly without pretreatment, it can be utilized extremely usefully in industrial applications.

REFERENCE SIGNS LIST 1 sludge (fuel)
2 combustion air
3 auxiliary fuel
4 secondary air
5 flue gas
10A, 10B $N_2O$ concentration analysis device
11 light source (light emission means)
12a, 12b window
13 light receiver (light reception means)
14 control device
14a light source control unit (wavelength control means)
14b signal analyzing unit ($N_2O$ concentration calculation means)
15a temperature measurement instrument (temperature measurement means)
100A, 100B sludge incinerator
101 incinerator main body
102 fluidized bed
103 freeboard
105 flue

The invention claimed is:
1. An $N_2O$ analysis device comprising:
light emission means for emitting laser light to flue gas containing $N_2O$, $H_2O$, and $CO_2$, the flue gas being at normal pressures and being not treated with any one of a dust removal and a dehumidification and a pressure reduction;
light reception means for receiving the laser light emitted to the flue gas;
wavelength control means for performing control such that a wavelength of the laser light emitted by the light emission means is in a 3.84 to 4.00 µm band; and

N₂O concentration calculation means for calculating a concentration of N₂O by means of infrared spectroscopy, using the laser light received by the light reception means and the laser light controlled by the wavelength control means.

2. The N₂O analysis device according to claim 1, wherein the wavelength control means performs control such that the wavelength of the laser light is 3.9034 to 3.9060 μm, 3.9090 to 3.9116 μm, or 3.9122 to 3.9148 μm.

3. The N₂O analysis device according to claim 1, wherein the wavelength control means performs control such that the wavelength of the laser light is 3.9047 μm, 3.9103 μm, or 3.9135 μm.

4. The N₂O analysis device according to claim 1, wherein the light emission means includes a nonlinear optical crystal, generates, by means of difference frequency generation using inputs of laser light with a wavelength of $\lambda_1$ and laser light with a wavelength of $\lambda_2$, laser light with a wavelength of $\lambda_3$ satisfying $1/\lambda_3 = 1/\lambda_1 - 1/\lambda_2$, and outputs the laser light with the wavelength of $\lambda_3$.

5. The N₂O analysis device according to claim 1, further comprising
temperature measurement means for measuring a temperature of the flue gas, wherein
the N₂O concentration calculation means calculates the concentration of N₂O by means of the infrared spectroscopy, using also the temperature of the flue gas measured by the temperature measurement means.

6. The N₂O analysis device according to claim 1, further comprising
sampling means for sampling the flue gas, wherein
the light emission means emits the laser light to the flue gas sampled by the sampling means.

7. The N₂O analysis device according to claim 6, further comprising
heating means for heating the flue gas sampled by the sampling means.

8. An N₂O analysis method comprising:
emitting, by light emission means, laser light with a wavelength of 3.84 to 4.00 μm to flue gas containing N₂O, H₂O, and CO₂, the flue gas being at normal pressures and being not treated with any one of a dust removal and a dehumidification and a pressure reduction;
receiving the laser light emitted to the flue gas; and
calculating a concentration of N₂O by means of infrared spectroscopy, using the received laser light and the laser light which is controlled to be 3.84 to 4.00 μm.

9. The N₂O analysis method according to claim 8, wherein
the wavelength of the laser light emitted by the light emission means is controlled to be 3.9034 to 3.9060 μm, 3.9090 to 3.9116 μm, or 3.9122 to 3.9148 μm.

10. The N₂O analysis method according to claim 8, wherein
the wavelength of the laser light emitted by the light emission means is controlled to be 3.9047 μm, 3.9103 μm, 3.9135 μm.

11. The N₂O analysis method according to claim 8, wherein
equipment including a nonlinear optical crystal is used for the light emission means, the equipment generating, by means of difference frequency generation using inputs of laser light with a wavelength of $\lambda_1$ and laser light with a wavelength of $\lambda_2$, laser light with a wavelength of $\lambda_3$ satisfying $1/\lambda_3 = 1/\lambda_1 - 1/\lambda_2$, and outputting the laser light with the wavelength of $\lambda_3$.

12. The N₂O analysis method according to claim 8, further comprising:
measuring a temperature of the flue gas; and
calculating the concentration of N₂O by means of the infrared spectroscopy, using also the measured temperature of the flue gas.

13. The N₂O analysis method according to claim 8, wherein the flue gas to which the laser light is emitted is sampled.

14. The N₂O analysis method according to claim 13, wherein
the sampled flue gas is heated.

* * * * *